US00PP23732P2

(12) United States Plant Patent
von Danwitz

(10) Patent No.: US PP23,732 P2
(45) Date of Patent: Jul. 9, 2013

(54) POINSETTIA PLANT NAMED 'RUBY FROST'

(50) Latin Name: *Euphorbia pulcherrima*
Varietal Denomination: Ruby Frost

(75) Inventor: Marita von Danwitz, Toenisvorst (DE)

(73) Assignee: Syngenta Crop Protection AG, Basel (CH)

( * ) Notice: Subject to any disclaimer, the term of this patent is extended or adjusted under 35 U.S.C. 154(b) by 417 days.

(21) Appl. No.: 12/799,106

(22) Filed: Apr. 19, 2010

(51) Int. Cl.
*A01H 5/00* (2006.01)

(52) U.S. Cl.
USPC ..... Plt./303

(58) Field of Classification Search
USPC ..... Plt./303
See application file for complete search history.

*Primary Examiner* — Wendy C Haas
(74) *Attorney, Agent, or Firm* — Joshua L. Price

(57) ABSTRACT

A new Poinsettia plant named 'Ruby Frost,' particularly distinguished by the variegated red and white bract color, medium sized inflorescences held well above the foliage canopy, medium to deep green foliage that are ovate to oak-shaped bracts and leaves with pointed lobes, medium sized, well-branched and mounding plant habit, mid-season flowering response, and good keeping quality of foliage and bracts.

1 Drawing Sheet

Latin name of the genus and species of the plant claimed: *Euphorbia pulcherrima.*

Varietal denomination: 'Ruby Frost'.

BACKGROUND OF THE NEW PLANT

The present invention comprises a new Poinsettia, botanically known as *Euphorbia pulcherrima* and hereinafter referred to by the variety name 'Ruby Frost.'

'Ruby Frost' is a product of a planned breeding program. The new cultivar 'Ruby Frost' has variegated red and white bract color, medium sized inflorescences held well above the foliage canopy, medium to deep green foliage that are ovate to oak-shaped bracts and leaves with pointed lobes, medium sized, well-branched and mounding plant habit, mid-season flowering response, and good keeping quality of foliage and bracts.

'Ruby Frost' originates from a hybridization made in March 2006 in a controlled breeding program in Toenisvorst, Germany. 'Ice Punch', U.S. Plant Pat. No. 19,504, is a parent to 'Ruby Frost'. The other parent is unknown.

The resulting seeds were sown in the summer of 2006 and 'Ruby Frost' was selected as one flowering plant within the progeny of the stated cross in December 2006 in a greenhouse in Toenisvorst, Germany.

The first act of asexual reproduction of 'Ruby Frost' was accomplished when propagation was made by propagating shoot tips from the initial selection in the early spring of 2007. These shoot tips were rooted and grown out.

Shoot tips from the original clone were grafted in June 2007 in order to improve the branching ability. Cuttings from the successfully grafted stems were rooted during summer 2007, and were cultivated for the first time, through small trial during the fall and winter of 2007.

Horticultural examination of this variety continued through the fall of 2008, with cuttings of the grafted plants initiated in the summer/fall of 2008 in Toenisvorst, Germany, and continuing thereafter on a larger scale, has demonstrated that the combination of characteristics as herein disclosed for 'Ruby Frost' are firmly fixed and are retained through successive generations of asexual reproduction.

A Plant Breeder's Right for this cultivar was applied for in the European Union on Sep. 12, 2008. 'Ruby Frost' has not been made publicly available more than one year prior to the filing of this application.

'Ruby Frost' has not been observed under all possible environmental conditions. The phenotype may vary significantly with variations in environment such as temperature, light intensity and day length.

BRIEF DESCRIPTION OF THE NEW VARIETY

The accompanying photographic drawing shows typical flower and foliage characteristics of 'Ruby Frost' with colors being as true as possible with an illustration of this type. The photographic drawing shows a flowering potted plant of the new variety and is about 4 months of age. The plant was grown in Hillscheid, Germany, in the fall of 2009.

DETAILED BOTANICAL DESCRIPTION

The measurements were taken on Dec. 5, 2009 on about 20 week old plants grown in a greenhouse in Hillscheid, Germany. Culture of these plants had started in late July (Week 30) 2009 with planting of rooted cuttings into 14 cm pots and terminal pinching about 2 weeks later. The plants were grown on benches in a green house under natural day light (no black cloth to initiate earlier flowering) and at moderately warm temperature of 18° C. for the bench heating.

Color Chart used: Royal Horticultural Society Colour Chart (R.H.S.) 2001

BRIEF SUMMARY OF INVENTION

The following observations, measurements, and comparisons describe plants grown in Toenisvorst and Hillscheid, Germany. The following traits have been repeatedly observed and are determined to be basic characteristics of the new variety. The combination of these characteristics distinguishes this Poinsettia plant as a new and distinct variety.

DIFFERENCES BETWEEN THE NEW VARIETY 'RUBY FROST' AND SIMILAR VARIETIES

In comparison to 'Ice Punch' (U.S. Plant Pat. No. 19,504), 'Ruby Frost' has a somewhat more diffuse red and pale pink pattern, spread over nearly the whole bract blade, while bracts of 'Ice Punch' have a narrower white center and red margins. Furthermore, 'Ruby Frost' has somewhat less deep green foliage color, and generally more compact plant habit.

In comparison to 'Marblestar' (U.S. Plant Pat. No. 9,685), with salmon pink and cream white edged bracts, 'Ruby Frost' displays a different kind of bract variegation, with the deepest reddish hue at margins and somewhat faded color towards the center and between the veins. Furthermore, both bracts and leaves of 'Ruby Frost' develop many smaller or larger pointed lobes, while bracts and leaves of 'Marblestar' have a more regular ovate to elliptical shape nearly without any lobes.

Plant:

*Form, growth and habit*.—Well branched with the branches slanting upright.
*Plant height* (*from top of soil*).—About 21-25 cm.
*Plant width*.—38-42 cm.
*Number of branches*.—7 on average.
*Number of inflorescences*.—6-7 per plant.

Stem:

*Color of stem*.—RHS 137D to RHS143A; at the tip somewhat lighter, RHS 143B to RHS143C, with no anthocyanins.
*Length of stem*.—14-17 cm.
*Diameter*.—0.5-0.7 cm.
*Length of internodes*.—1.5-2.5 cm.
*Texture*.—Smooth, glabrous.

Foliage:

*Arrangement*.—Alternate.
*Quantity per branch*.—About 5-7 leaves.
*Quantity of leaves per plant*.—About 45-50.
*Aspect*.—Most petioles are horizontally directed, while the leaf blades slant somewhat downwards.
*Immature leaf, color upper surface*.—RHS 143A.
*Immature leaf, color lower surface*.—RHS 144B.
*Mature leaf, color upper surface*.—RHS 137A to RHS137B.
*Mature leaf, color lower surface*.—RHS 137D.
*Leaf length*.—10.5-11.5 cm.
*Leaf width*.—7.5-9.5 cm.
*Shape*.—Roughly ovate to oak-shaped with relatively many, but not very large lobes, the lobes are somewhat irregular in shape.
*Base shape*.—Obtuse to acute.
*Apex shape*.—Acuminate.
*Margin*.—Mostly entire, crenation may appear in some areas.
*Texture*.—Smooth, apart from the protruding veins on the underside, glabrous on both surfaces.
*Arrangement of veins*.—Pinnate.
*Color of veins, upper surface*.—Mainly indistinct, near RHS 143C, possibly reddish at the base RHS 47A, fading towards the leaf tip.
*Color of veins, lower surface*.—RHS 145C.
*Petiole color, upper surface*.—RHS 145B to RHS 145C at leaf base: RHS 53D and RHS 51D lines may occur.
*Petiole color, lower surface*.—RHS 145A to RHS145B.
*Petiole length*.—Mostly 4.5-6.5 cm.
*Diameter of petiole*.—0.2-0.3 cm.
*Texture upper and lower surfaces*.—Smooth, glabrous.

Inflorescence:

*Type*.—Terminal cyme with surrounding whorl of colored bracts, usually one inflorescence per stem.
*Number of inflorescences per plant*.—6-7.
*Flowering, botanically* (*opening of the stamina, shedding of pollen*).—Around December 1.
*Flowering, commercially* (*sufficiently colored bracts*).—Mid to late November.
*Flowering response time*.—About 7.5-8 weeks from equinox.
*Duration of flowering*.—Depends on light and environment, at least 4-6 weeks of 'shelf' life.
*Fragrance*.—Absent.
*Shape of inflorescence*.—Nearly flat, rosette-like arrangement with the bracts somewhat overlapping.
*Diameter of inflorescence*.—23-25 cm.
*Inflorescence, vertical diameter*.—2.0-3.0 cm.
*Number of completely colored bracts per inflorescence* (*sized over 2 cm*).—11-15.

(Single) bract:

*Shape*.—Ovate to weakly oak-leaf-shaped, with both rounded and pointed lobes.
*Apex*.—Acuminate.
*Bract, base*.—Acute to obtuse.
*Bract, length of blade*.—9.5-10.3 cm, younger bracts diminishing in size.
*Width*.—6.5-8.0 cm.
*Overall color*.—Reddish with lighter tones between veins and near mid rib; the intensity of color is distinctly dependent from temperature, lightest tones under cool conditions.
*Bract color, upper side*.—Margins between RHS 46C and RHS 46D, while the main part of the bract blade is RHS 47A to 47B interspersed with RHS 52B to RHS 46D; Near the midrib and at apices is RHS 49A to RHS 49B.
*Bract color, lower side*.—Margins RHS 46C to RHS 46D, at center varying from RHS 52B to RHS46D.
*Vein color, upper surface*.—RHS 46B to RHS 46C.
*Vein color, lower surface*.—RHS 145B to RHS 145C, fading towards tip to RHS 150D.
*Texture, both surfaces*.—Slightly rugose, glabrous.
*Bract petiole, length*.—About 1.5-3.0 cm.
*Bract petiole diameter*.—0.2 cm.
*Petiole color, upper surface*.—RHS 45B or RHS 27B.
*Petiole color, lower surface*.—RHS 145B to RHS 158D.

Cyme (true inflorescence):

*Cyme, diameter*.—2.5-3.0 cm.
*Number of cyathia*.—10-20, borne in a tight cluster.
*Cyathium, shape*.—Ovate.
*Cyathium, diameter*.—0.4 cm.
*Cyathium, length*.—0.5 cm.
*Color*.—RHS 143C; top is RHS 46A to RHS 46B.
*Peduncle length*.—0.3 cm.
*Peduncle diameter*.—0.2-0.3 cm.
*Peduncle color*.—RHS 143C.
*Nectar cups per cyathium*.—One or two.
*Nectur cup, width*.—0.3-0.4 cm.
*Nectar cup, color*.—RHS 21A or RHS 32A.

Reproductive organs:

*Stamen* (*actually reduced male florets*).—Usually in a bunch of 15-20 at the top of the cyathium.

*Shape*.—Strap-like.
*Filament length*.—0.2-0.3 cm.
*Filament color*.—RHS 46B.
*Anther color*.—RHS 11A.
*Anther diameter*.—0.1 cm.
*Pollen quantity*.—Moderate.
*Pollen color*.—RHS 12A.
*Pistils* (*actually female flowers*).—None observed.

Fertility/seed set: No seed set observed.
Disease/pest resistance: Disease/pest resistance has not been observed on this hybrid.

What is claimed is:

1. A new and distinct variety of Poinsettia plant named 'Ruby Frost,' substantially as illustrated and described herein.

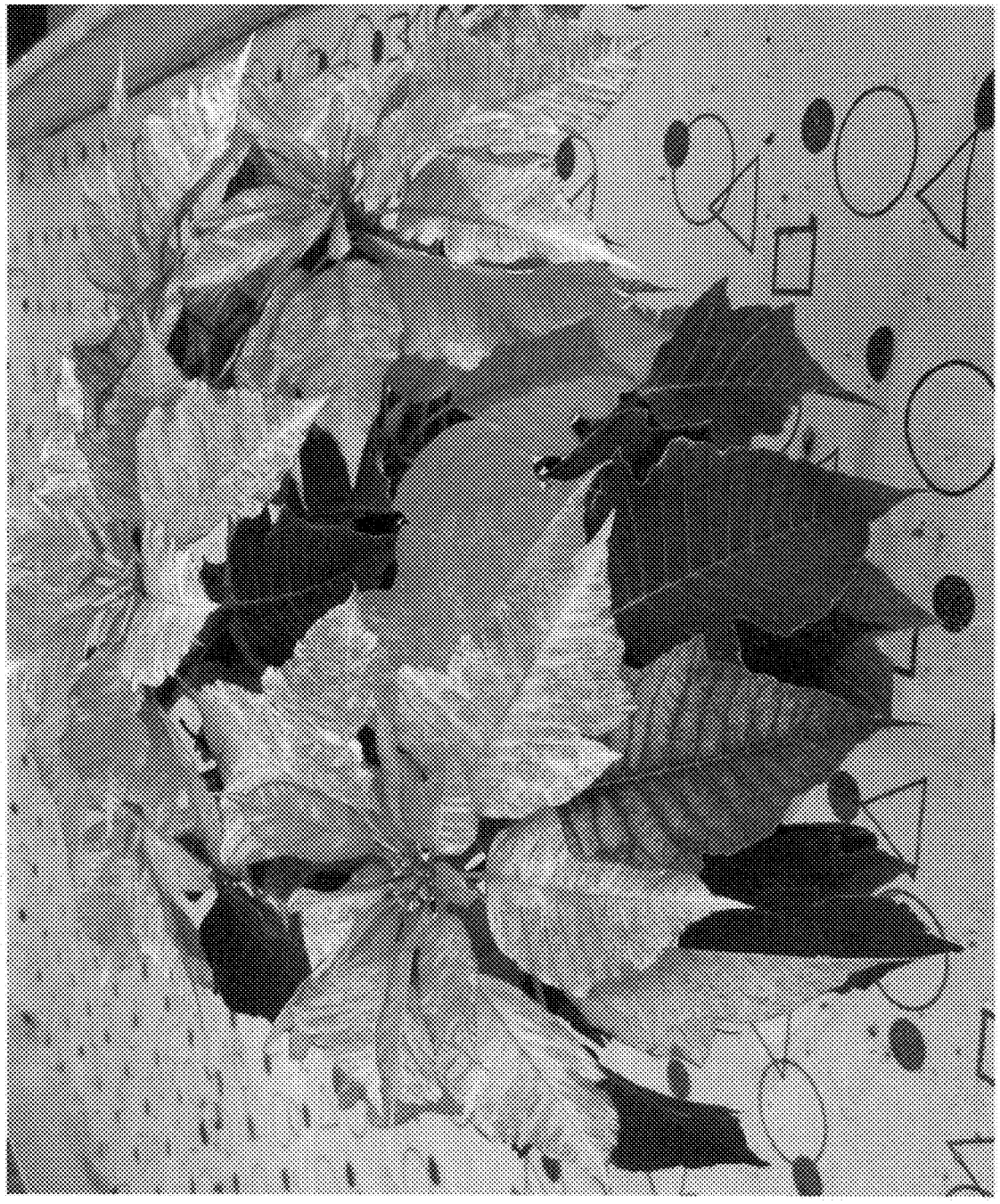

* * * * *